(12) United States Patent
Chang et al.

(10) Patent No.: US 10,258,273 B2
(45) Date of Patent: Apr. 16, 2019

(54) REAL-TIME CONTINUOUS STRESS MONITORING USING WEARABLE DEVICES

(71) Applicant: INTERNATIONAL BUSINESS MACHINES CORPORATION, Armonk, NY (US)

(72) Inventors: Hung-yang Chang, Scarsdale, NY (US); Tian Hao, White Plains, NY (US); Kun Lin, Montgomery, MD (US); Xinxin Zhu, Croton on Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 7 days.

(21) Appl. No.: 15/598,565

(22) Filed: May 18, 2017

(65) Prior Publication Data

US 2018/0333090 A1 Nov. 22, 2018

(51) Int. Cl.
*A61B 5/00* (2006.01)
*A61B 5/16* (2006.01)
*A61B 5/024* (2006.01)

(52) U.S. Cl.
CPC ............ *A61B 5/165* (2013.01); *A61B 5/0015* (2013.01); *A61B 5/02438* (2013.01); *A61B 5/681* (2013.01); *A61B 5/721* (2013.01); *A61B 5/7278* (2013.01); *A61B 5/742* (2013.01)

(58) Field of Classification Search
CPC ....... A61B 5/024; A61B 5/02405; A61B 5/11; A61B 5/1118; A61B 5/165; A61B 5/721
See application file for complete search history.

(56) References Cited

U.S. PATENT DOCUMENTS

| | | | |
|---|---|---|---|
| 8,527,213 B2 | 9/2013 | Kailas et al. | |
| 9,171,131 B2 | 10/2015 | Meyer et al. | |
| 2010/0324427 A1* | 12/2010 | Devot ................. | A61B 5/0205 600/484 |
| 2014/0142397 A1 | 5/2014 | Bedrosian et al. | |
| 2014/0247155 A1 | 9/2014 | Proud | |

(Continued)

OTHER PUBLICATIONS

H. Lu et al., "Stresssense: Detecting stress in unconstrained acoustic environments using smartphones," ACM Conference on Ubiquitous Computing, 2012, pp. 351-360.

(Continued)

*Primary Examiner* — Scott M. Getzow
(74) *Attorney, Agent, or Firm* — Cantor Colburn LLP; Vazken Alexanian

(57) ABSTRACT

Embodiments of the present invention are directed to a computer-implemented method for stress monitoring. Methods include receiving, by a processor, a plurality of user stress labels corresponding to a plurality of events. Methods also include determining an individualized stress profile based at least in part upon the user stress labels. Methods also include receiving heart rate sensor data from a wearable device. Methods also include extracting a cardiovascular feature from the heart rate sensor data. Methods also include determining a stress index based at least in part upon the individualized stress profile and the cardiovascular feature. Methods also include outputting the stress index.

25 Claims, 11 Drawing Sheets

(56) References Cited

U.S. PATENT DOCUMENTS

2014/0249853 A1 9/2014 Proud et al.
2014/0297299 A1 10/2014 Lester, IV

OTHER PUBLICATIONS

J. A. Healey et al., "Detecting stress during real-world driving tasks using physiological sensors," IEEE Transactions on intelligent transportation systems, vol. 6, No. 2, 2005, pp. 156-166.

K. Hovsepian et al., "cStress: towards a gold standard for continuous stress assessment in the mobile environment." ACM International Joint Conference on Pervasive and Ubiquitous Computing, 2015, pp. 493-504.

W. Liao et al., "A real-time human stress monitoring system using dynamic Bayesian network," 2005 IEEE Computer Society Conference on Computer Vision and Pattern Recognition, CVPR'05, 2005, 8 pages.

* cited by examiner

REAL-TIME CONTINUOUS STRESS MONITORING USING WEARABLE DEVICES

BACKGROUND

The present invention generally relates to stress monitoring, and more specifically, to real-time continuous stress monitoring using consumer wearable devices.

Unmanaged sustained high levels of stress can lead to serious adverse consequences. For instance, stress is a leading risk factor for many common chronic medical conditions such as cardiovascular disease, diabetes, and depression. Moreover, evidence of the adverse impact of stress on health is increasing. Stress response can be highly individualistic and, thus, monitoring and assessing the impact of stress are not suited to a "one-size-fits all" approach. What qualifies as a stressor and the perception of what amounts to stress can vary widely from one individual to the next. For example, some people, but not all people, become stressed in public speaking situations. Moreover, the degree to which a stressor negatively impacts an individual can be highly personalized. Thus, effective characterization of stress in daily life presents several challenges.

Stress assessment techniques based upon questionnaires and self-reporting can provide some information on the stress level of an individual to aid in stress management. However, such techniques provide information of a particular time span, rather than the dynamic progression of stress over time.

Stress monitoring and management studies employ a variety of equipment. In some cases, specialized devices, such as skin conductance sensors, can provide detailed and/or dynamic information regarding stress levels. However, such equipment can be specialized, costly, and in some cases invasive. Thus, stress monitoring and management studies that seek to obtain information concerning stress over a time span can require a specialized laboratory setting or can be cumbersome, impractical, or cost-prohibitive for an individual to use.

SUMMARY

Embodiments of the present invention are directed to a computer-implemented method for stress monitoring. A non-limiting example of the computer-implemented method includes receiving, by a processor, a plurality of user stress labels corresponding to a plurality of events. The method also includes determining, by the processor, an individualized stress profile based at least in part upon the user stress labels. The method also includes receiving, by the processor, heart rate sensor data from a wearable device. The method also includes extracting, by the processor, a cardiovascular feature from the heart rate sensor data. The method also includes determining, by the processor, a stress index based at least in part upon the individualized stress profile and the cardiovascular feature. The method also includes outputting, by the processor, the stress index to the wearable device. Such embodiments can provide personalized stress management to a user that is convenient and can be implemented on a daily basis.

Embodiments of the invention are directed to a computer program product for stress monitoring, the computer program product including a computer readable storage medium having program instructions embodied therewith. The program instructions are executable by a processor to cause the processor to perform a method. A non-limiting example of the method includes receiving a plurality of user stress labels corresponding to a plurality of events. The method also includes determining an individualized stress profile based at least in part upon the user stress labels. The method also includes receiving heart rate sensor data from a wearable device. The method also includes extracting a cardiovascular feature from the heart rate sensor data. The method also includes determining a stress index based at least in part upon the individualized stress profile and the cardiovascular feature. The method also includes outputting the stress index to the wearable device. Such embodiments can provide personalized stress management to a user that is convenient and can be implemented on a daily basis.

Embodiments of the present invention are directed to a processing system for monitoring stress. A non-limiting example of the system includes a processor in communication with one or more types of memory. The processor is configured to receive a plurality of user stress labels corresponding to a plurality of events. The processor is also configured to determine an individualized stress profile based at least in part upon the user stress labels. The processor is also configured to receive heart rate sensor data from a wearable device. The processor is also configured to extract a cardiovascular feature from the heart rate sensor data. The processor is also configured to determine a stress index based at least in part upon the individualized stress profile and the cardiovascular feature. The processor is also configured to output the stress index to the wearable device. Such embodiments can provide personalized stress management to a user that is convenient and can be implemented on a daily basis.

Embodiments of the present invention are directed to a system for monitoring stress. A non-limiting example of the system includes a wearable device. The wearable device can include a stress monitoring module including a heart rate sensor, an individualized stress profile, and a stress index engine, wherein the stress index engine is capable of determining a stress index for a user. The wearable device can also include a sample regulation module including a sampling schedule controller, wherein the sample schedule controller is capable of actuating the stress monitoring module. Such embodiments can provide personalized stress information in a convenient wearable device for individual stress management.

Embodiments of the present invention are directed to a computer-implemented method for stress monitoring. A non-limiting example of the computer-implemented method includes activating, by a processor, a stress sampling based upon a sampling schedule. The method can also include determining, by the processor, a heart rate variability based at least in part upon heart rate sensor data. The method can also include determining, by the processor, an individualized stress profile based at least in part upon a user stress input. The method can also include determining, by the processor, a continuous stress index based at least in part upon individualized stress profile and heart rate variability. The method can also include receiving motion sensor data of a user. The method can also include modifying the sampling schedule based at last in part upon a determination that a user motion is likely to lead to artifacts. Such embodiments can provide relevant stress information to a user over extended periods of time without excessive power consumption.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
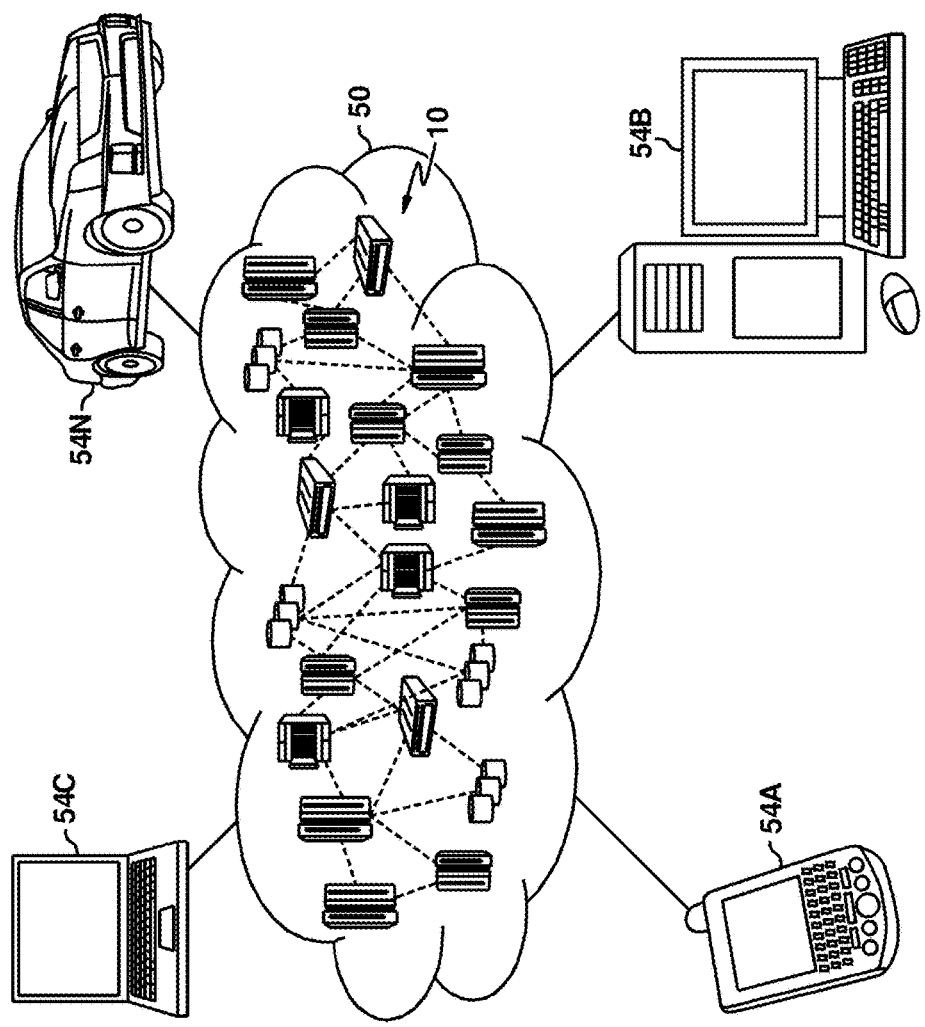
FIG. 1 depicts a cloud computing environment according to an embodiment of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
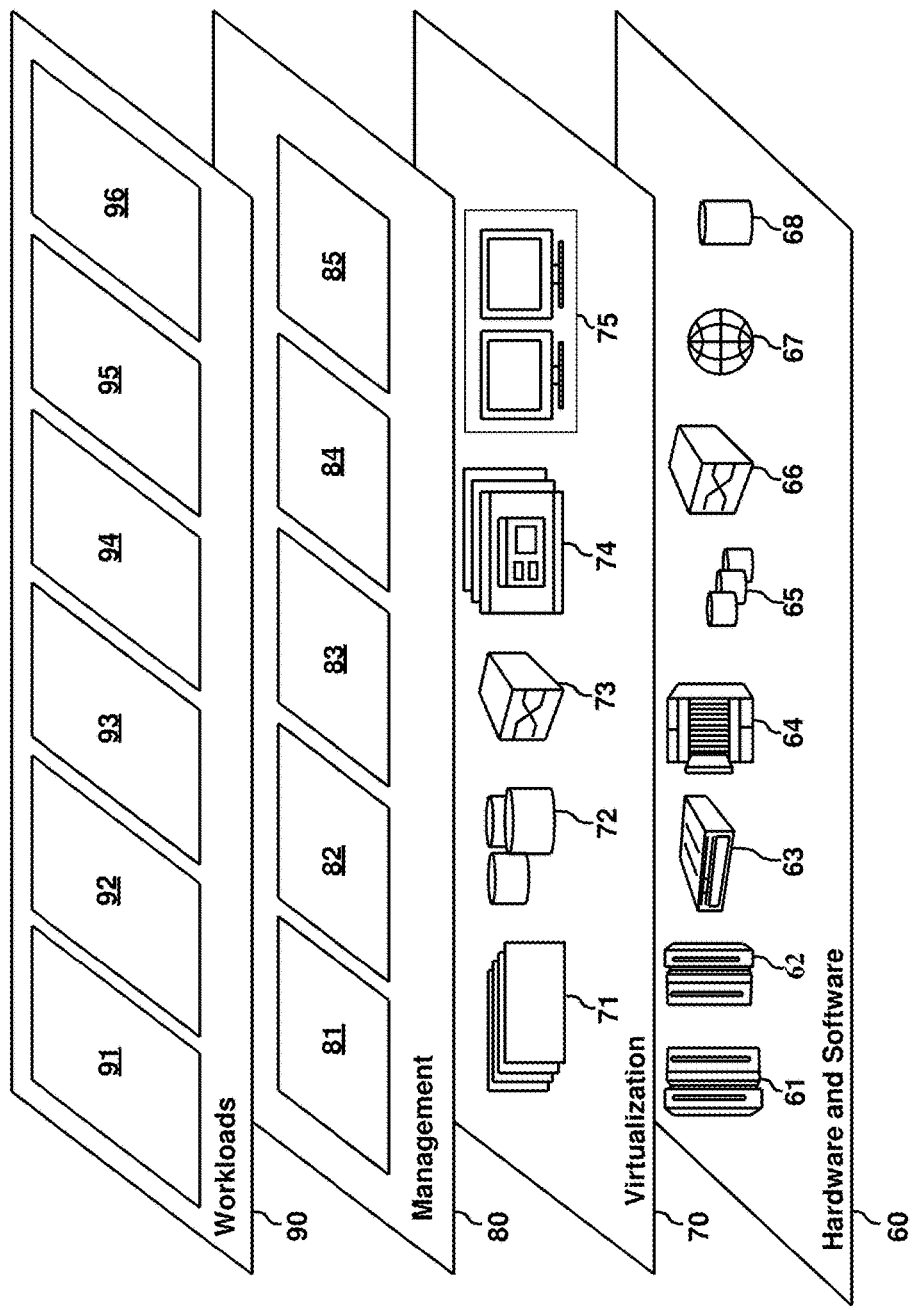
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments of the invention, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and real-time continuous stress monitoring 96.

Figure 3:
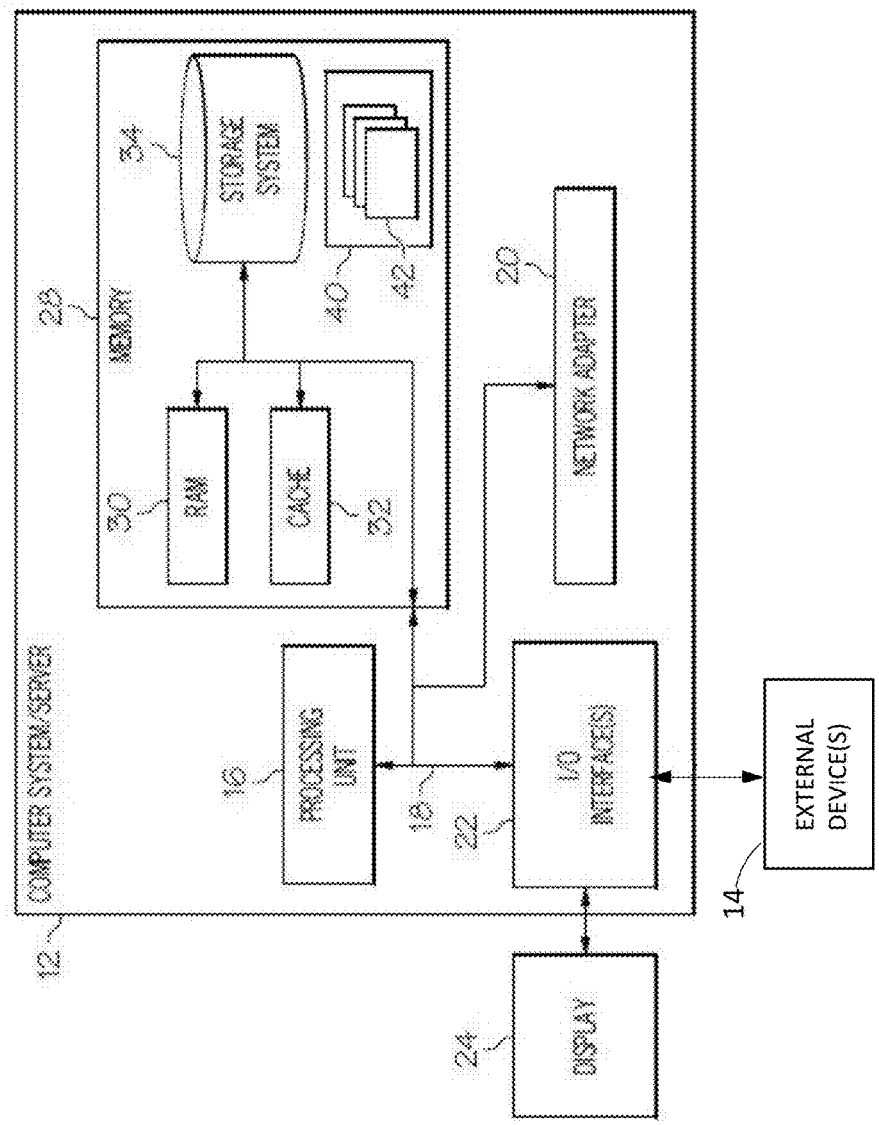
FIG. 3 depicts a block diagram illustrating one example of a processing system for practice of the teachings herein.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of technologies that are more specifically relevant to aspects of the invention, embodiments of the invention include systems, methods, and apparatuses for real-time, continuous stress monitoring using consumer wearable devices. The ability to continuously monitor and manage stress in real-time can allow users of commercially available wearable devices, such as smart watches, to effectively and efficiently manage their stress levels.

Practical methods for assessing and monitoring stress accessible to consumers could aid in the reduction of overall stress levels and improve the health of consumers. Individuals experience stress frequently in their daily lives. However, despite the adverse consequences of continuous stress or high stress levels, conventional methods of monitoring stress can lack the capability of fueling large-scale health analytics with continuous and long term stress data available to and practical for a general consumer.

Turning now to an overview of aspects of the invention, embodiments of the invention provide practical, continuous, unobtrusive, and/or personalized stress analysis and management. By providing ongoing stress analyses, embodiments of the invention can help users stay aware of their stress levels. Some embodiments of the invention can guide users to take effective and efficient actions to recover from elevated stress. Some embodiments of the invention allow smart device wearers to predict and prevent instances of high stress through intelligent planning of daily tasks with the aid of a cognitive stress pattern. Reduction and mitigation of high stress levels utilizing aspects of the present invention can contribute to the health and well-being of individuals.

Embodiments of the invention can include components of commercially available wearable technologies. For instance, smart watches can include heart rate sensors that can provide a measure of the variation in heartbeat of a wearer. It is known, for example, that heart rate variability (HRV) can be proportional to stress. In addition, embodiments of the invention can employ other indicators of stress, many of which can be included within or linked to a wearable device, in conjunction or instead of HRV to provide real-time stress monitoring.

Embodiments of the invention can sense one or more stress indicators on a continuous or periodic basis to provide a real-time assessment of the stress level of a user. Moreover, embodiments of the invention can be personalized to a user and adapt to a user's physiological response.

Figure 4B:
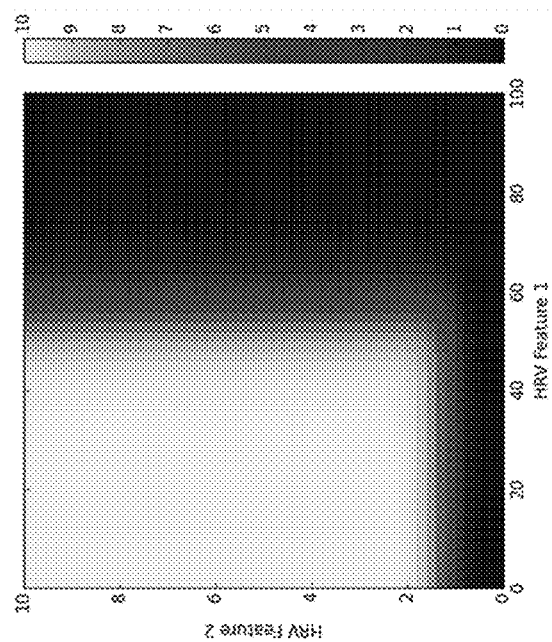
FIG. 4B depicts a stress profile for a user according to one or more embodiments of the present invention.
Figure 4A:
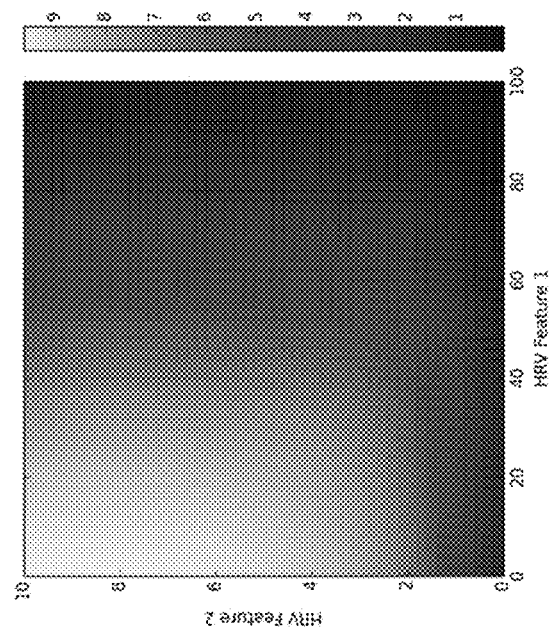
FIG. 4A depicts a stress profile for a user according to one or more embodiments of the present invention.

Difficulties with conventional analysis and monitoring of stress arise from the individualistic nature of stress response. For example, FIGS. 4A and 4B illustrate stress profiles for two different users based upon self-reporting and chart heart rate variability (HRV) for two different features in the horizontal plane versus self-reported stress level on a 10 point scale. FIG. 4A depicts the stress profile for user A, a young adult, and FIG. 4B depicts the stress profile for user B, an elderly adult. As is shown, with the same set of physiological features, user A and user B report different levels of stress.

Figures 5A, 5B:
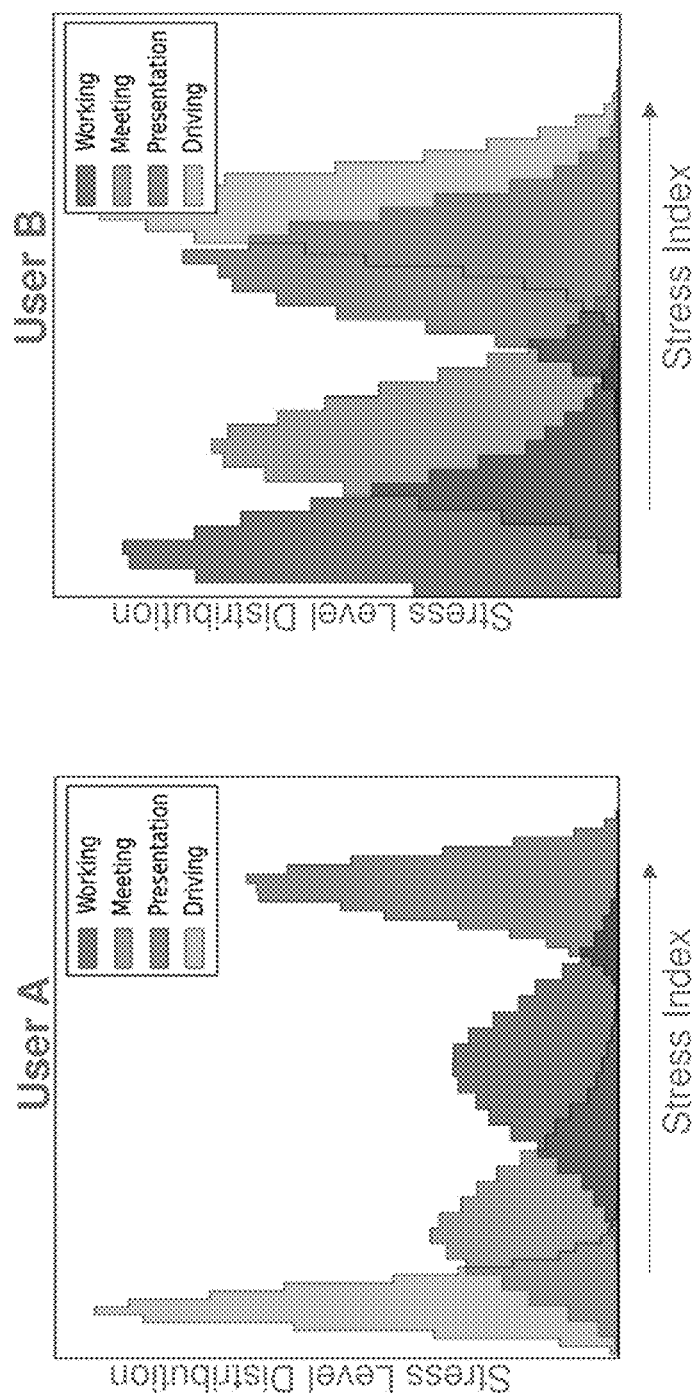
FIG. 5A depicts a stress profile for a user according to one or more embodiments of the present invention.
FIG. 5B depicts a stress profile for a user according to one or more embodiments of the present invention.

In addition to physiologic variability, the identity of stressors can vary from person to person. For instance, FIGS. 5A and 5B illustrate stress index versus stress level distribution of four different stressors for two different individuals. The stress profile of user A is depicted in FIG. 5A, and illustrates that, of the potential stressors working, meeting, presentation, and driving, user A experiences the highest stress when giving a presentation and the lowest stress when driving. The stress profile of user B is depicted in FIG. 5B and illustrates that, for this user, driving presents the highest stress and working presents the least stress of the four potential stressors.

Stress monitoring provided by embodiments of the invention can include analysis and interpretation of an individualized stress profile. The individualized stress profile can be created in advance of regular use and refined to adapt to a user's unique physiological response. Ongoing stress monitoring, in some embodiments of the invention, can take into account the individualized stress profile of a user to provide a personalized assessment for stress management. An individualized stress profile, for example, can correlate a user identified stressor with an initial cardiovascular feature level. For example, a baseline assessment can be made in some embodiments in a training mode to provide an individualized stress profile. In some embodiments of the invention, an individualized stress profile is created and modified on an ongoing basis, for example, by receiving periodic user input correlating identified stressors or stress levels with cardiovascular features or feature levels, such as a stress level and associated HRV.

Some embodiments of the invention include a feedback communication architecture for improved power consumption. For example, a tiered feedback communication architecture can increase the effectiveness of wearable devices while maintaining effective stress monitoring performance.

Figure 6:
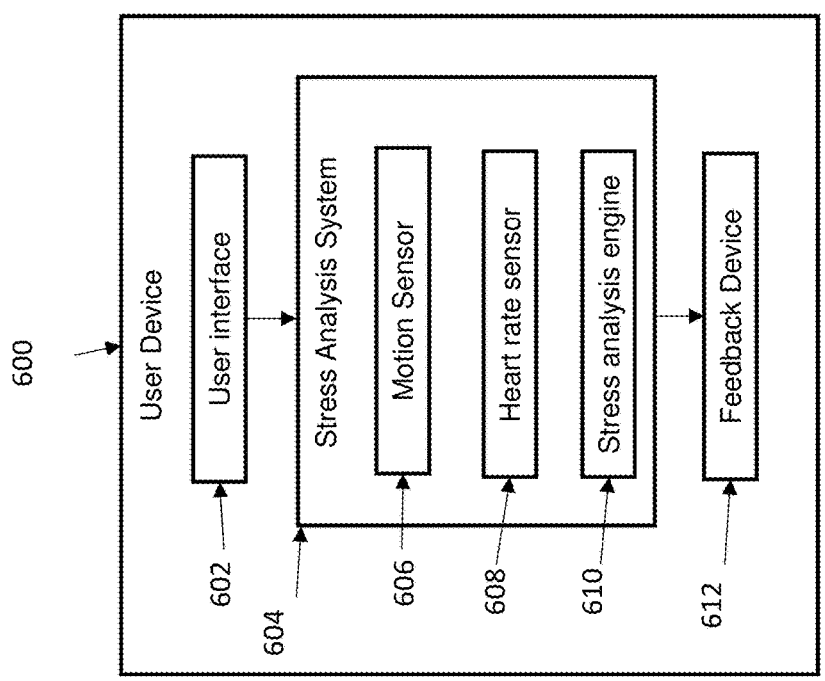
FIG. 6 depicts a block diagram illustrating an exemplary embodiment of the present invention.

Turning now to a more detailed description of embodiments of the invention, FIG. 6 depicts and exemplary device 600 for real-time continuous stress monitoring according to some embodiments of the invention. Device 600 can include a consumer wearable device, such as a smart watch, smart phone, or other consumer wearable device or system including a motion sensor, heart rate sensor, and microprocessor. In some embodiments of the invention, the device 600 is a smart watch.

The device 600 can include a user interface 602. The user interface can receive feedback from a user and can include, for instance, a smart watch display. The device can also include a stress analysis system 604. The stress analysis system can include, for example, a motion sensor 606, a heart rate sensor 608, and a stress analysis engine 610. The motion sensor can include, for instance, an accelerometer or a global positioning device. Stress analysis system can include any sensor that can be useful for detecting or predicting stress in an individual, such as temperature sensors, humidity sensors, ambient light sensors, and/or location sensors such as global positioning devices and accelerometers. The device 600 can also include a feedback device 612. The feedback device 612 can include, for instance, a smartwatch display or microphone, and can provide an output to a user pertaining to an actual or predicted stress level. The output can be visual, auditory, or haptic, and can include, for instance, graphic text or pictures, vibration, sounds, music, or verbal feedback. The output can include, for example, a current stress level or predicted stress level and any related information that could be helpful to a user in mitigating stress, such as time, location, activity, duration of stress, degree of stress, and/or cause or likely cause of stress. In some embodiments of the invention, the feedback device and the user interface are the same component. In some embodiments of the invention, the feedback device and the user interface are different components. In some embodiments of the invention, the feedback device and/or the user interface include a plurality of components, such as a combination of a display, microphone, and speaker.

Figure 7B:
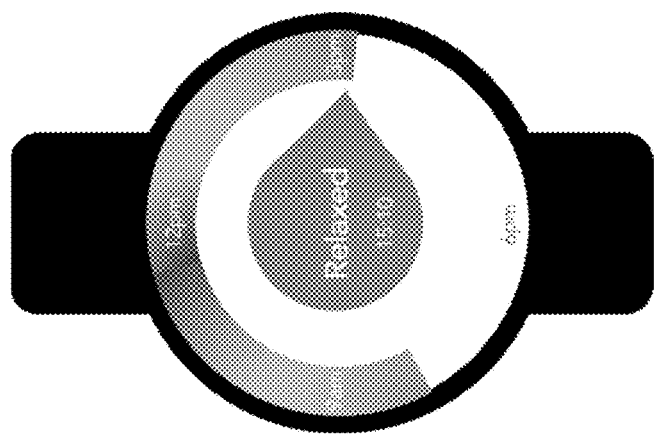
FIG. 7B depicts an example of an embodiment of the present invention.
Figure 7A:
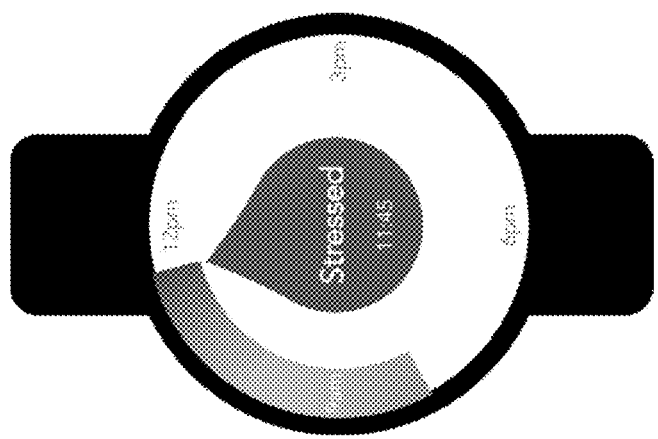
FIG. 7A depicts an example of an embodiment of the present invention.

FIGS. 7A and 7B illustrate an exemplary output display of an exemplary system according to embodiments of the disclosure. FIG. 7A depicts an exemplary graphic on a smart watch display indicating the wearer is stressed. FIG. 7B depicts an exemplary graphic indicating the wearer of a smart watch is relaxed.

In some embodiments of the invention, a device 600 can request user feedback at the user interface. For example, in some embodiments of the invention, a user provides feedback to train or personalize the system to that user, or to update or refine the personalization of the system. In some embodiments of the invention, a device 600 can request user feedback in connection with stress reporting or stress management.

Figure 8C:
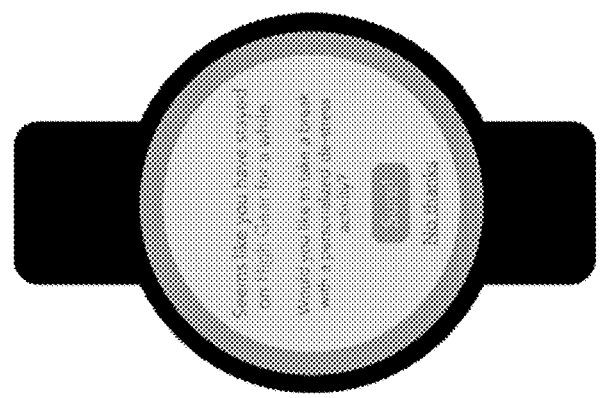
FIG. 8C depicts an example of an embodiment of the present invention.
Figure 8B:
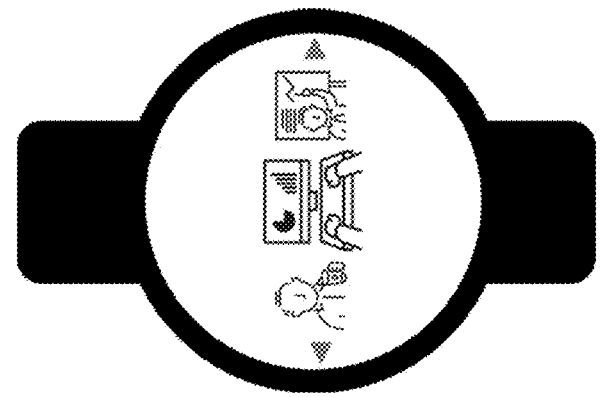
FIG. 8B depicts an example of an embodiment of the present invention.
Figure 8A:
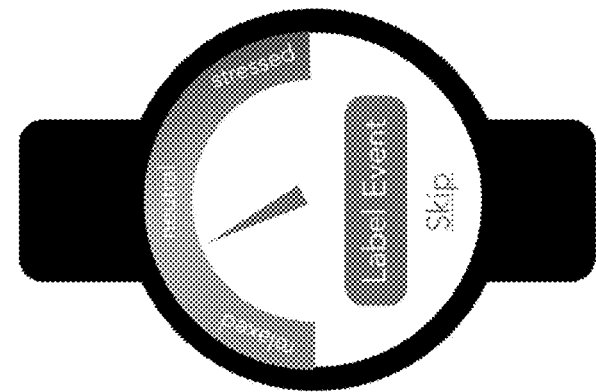
FIG. 8A depicts an example of an embodiment of the present invention.

FIGS. 8A-8C illustrate exemplary requests for user feedback at the user interface according to some embodiments of the invention. In some embodiments of the invention, a user interface can request user input for stress labeling. Stress labeling can include, for example, associating data, such as sensory data, with identifying information, such as a perceived stress level (FIG. 8A) or the activity associated with the data (FIG. 8B). In some embodiments of the invention the feedback at the user interface can assist with stress management, for instance by notifying the user of high stress and offering stress mitigation (FIG. 8C).

In some embodiments of the invention, a stress monitoring system includes a tiered approach for monitoring and assessment of stress. Some embodiments of the invention include a three-tiered system including a motion-aware tier, a stress-aware tier, and a context-aware tier. A three-tiered system can coordinate between the sampler and the monitor to provide enhanced accuracy in stress level monitoring with reduced power consumption.

Figure 9:
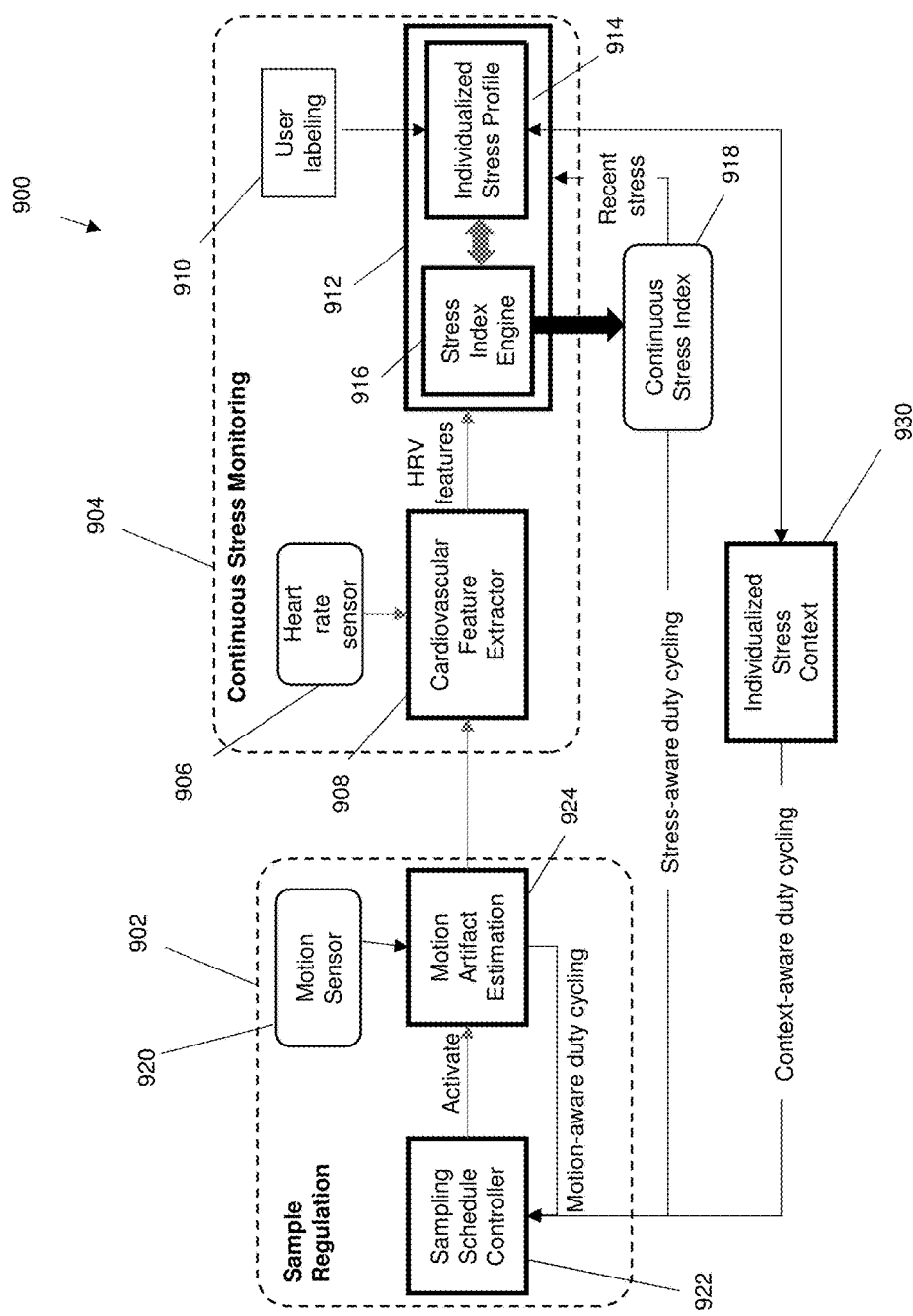
FIG. 9 depicts a block diagram illustrating an exemplary embodiment of the present invention.

FIG. 9 depicts an exemplary stress monitoring system 900 according to some embodiments of the invention. The system 900 can include a plurality of modules, including a stress monitoring module 904. The stress monitoring module 904 can perform operations associated with the stress-aware tier, for example, in a tiered module according to embodiments of the invention. The stress monitoring module 904 can include a heart rate sensor 906 in communication with a cardiovascular feature extractor 908. The cardiovascular feature extractor 908 can, for example, analyze input from the heart rate sensor 906 to determine a heart rate and heart rate variability or other heart rate features useful in the analysis or monitoring of stress and can provide one or more heart rate features, such as heart rate variability, to a stress monitoring hub 912. The stress monitoring module 904 also includes a user labeling input 910. User labeling input 910 includes user-self reporting data. A user can input perception of stress or stress severity, for instance, in real time or periodically, such as at the end of a day. The user labeling input 910 can include textual, graphic, auditory, or haptic input. For instance, in some embodiments of the invention, a user can tap a smart watch display screen to indicate the user is perceiving stress. The user labeling 910 can provide input to a stress monitoring hub 912 that includes an individualized stress profile 914 and a stress index engine 916. The stress index engine 916 can analyze data from the individualized stress profile 914 and cardiovascular feature extractor 908 to generate a continuous stress index 918. The continuous stress index 918 can include, for example, a real-time indication of stress and relative stress severity personalized to an individual user. In some embodiments of the invention, the stress index provides a real-time determination of the presence or absence of an unhealthy stress level (i.e., a stress level that could be attributed to an unhealthy condition by a medical professional). For example, an individualized stress index can be obtain via tight coupling from the individualized stress profile and the stress engine. In some embodiments of the invention, the continuous stress index 918 can communicate with the stress monitoring hub 912, for example to update or modify an individualized stress profile 914.

In some embodiment of the invention, the individualized stress profile 914 includes a personalized profile based upon user psychological and physiological features, user stress level distributions across different stressors, or both.

In some embodiments of the invention, the system 900 includes a sample regulation module 902. The sample regulation module can determine how frequently the stress sensor should sample. In some embodiments of the invention, the sample regulation module 902 uses motion, stress, and/or context to determine a sampling schedule. The sample regulation module 902 can preserve power to a system to enable stress sampling throughout the day and/or can increase a sampling schedule to provide timely feedback to a user for stress management. In some embodiments of the invention, the sampling regulator 902 includes a motion sensor 920. The motion sensor 920 can provide input to a motion artifact estimation module 924. The motion artifact estimation module 924 can, for example, identify periods of motion that are likely to corrupt stress related data. For example, when a user is exercising, an elevated heart rate is likely to obscure any heart rate-related stress information. Thus, continuous stress monitoring using heart rate sensor data during such periods can unnecessarily waste system resources. In some embodiments of the invention, motion artifact estimation module 924 can activate or inactivate one or more components of the stress monitoring system. In some embodiments of the invention, the motion artifact estimation module 924 activates or inactivates the cardiovascular feature extractor 908. The motion artifact estimation module 924 can also receive information from and provide information to a sampling schedule controller 922 to increase or decrease a sampling schedule as appropriate in motion-aware duty cycling.

The sampling schedule controller 922 can control the sampling schedule of the system 900. For example, the sampling schedule controller 922 can control the sampling schedule based upon a pre-conceived periodic sampling schedule, or based upon other factors including contextual data.

In some embodiments of the invention, the sampling schedule controller can receive contextual data from an individualized stress context module 930. The individualized stress context 930 and individualized stress profile 914 can interact, for example, to signal a context in which the user is likely to experience stress. For instance, contextual information in the individualized stress context module 930 can indicate that a user is at an airport and, based upon the individualized stress profile 914, is likely to become stressed at the airport, for example due to travel anxiety. Such contextual information can be used in context-aware duty cycling to modify a sampling schedule in the sampling schedule controller 922 to increase or decrease the sampling period as appropriate.

In some embodiments of the invention, sampling schedule controller 922 can increase or decrease a sampling schedule based upon a continuous stress index 918 in stress-aware duty cycling. For example, when an elevated stress level is detected, the system 900 can increase the sampling frequency to provide users with timely feedback.

Figure 10:
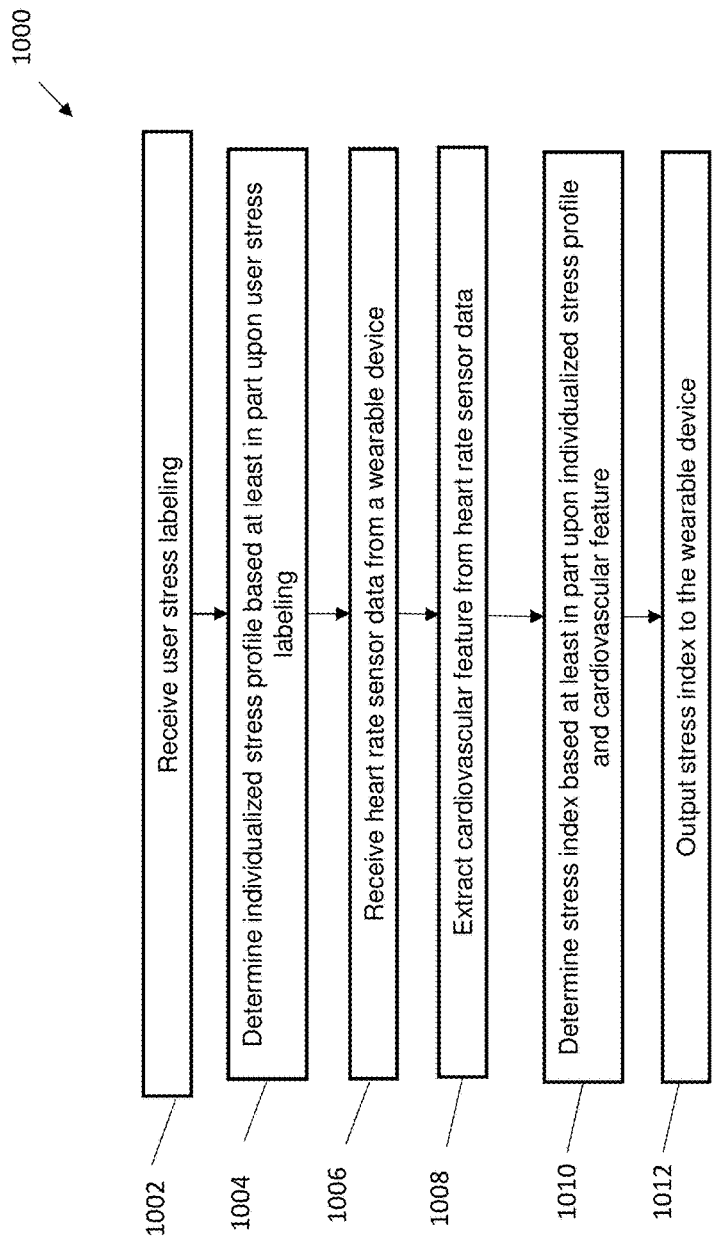
FIG. 10 depicts a flow diagram illustrating an exemplary embodiment of the present invention.

FIG. 10 depicts a flow diagram of an exemplary method 1000 of monitoring stress according to one or more embodiments of the present invention. The exemplary method 1000 includes, as shown at block 1002, receiving a user stress labeling. The exemplary method 1000 also includes, as shown at block 1004, calculating an individualized stress profile based at least in part upon the user stress labeling. The exemplary method 1000 also includes, as shown at block 1006, receiving heart rate sensor data from a wearable device. The exemplary method 1000 also includes, as shown at block 1008, extracting cardiovascular feature data from heart rate sensor data. The exemplary method 1000 also includes, as shown at block 1010, calculating a stress index based at least in part upon the individualized stress profile and cardiovascular feature. The method 1000 also includes, as shown at block 1012, outputting a stress index to the wearable device.

Figure 11:
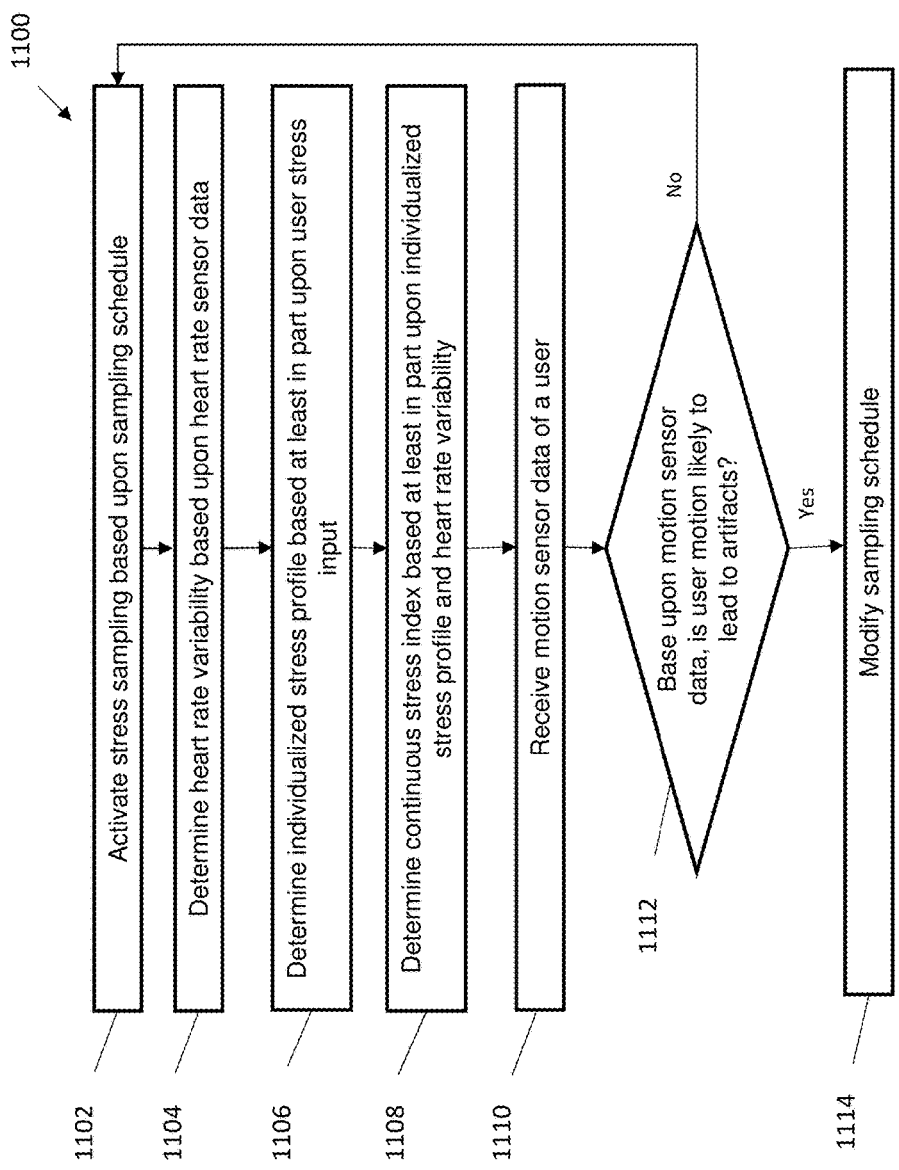
FIG. 11 depicts a flow diagram illustrating an exemplary embodiment of the present invention.

FIG. 11 depicts a flow diagram of another exemplary method 1100 of monitoring stress according to one or more embodiments of the present invention. The exemplary method 1100 includes, as shown at block 1102, activating a stress sampling based upon a sampling schedule. The method 1100 also includes, as shown at block 1104, determining a heart rate variability based at least in part upon heart rate sensor data. The exemplary method 1100 includes, as shown at block 1106, determining an individualized stress profile based at least in part upon a user stress input. The exemplary method 1100 also includes, as shown at block 1108, calculating a continuous stress index based at least in part upon an individualized stress profile and heart rate variability. The exemplary method 1100 includes, as shown at block 1110, receiving motion sensor data of a user. The exemplary method 1100 includes, as shown at decision block 1112, determining, based upon motion sensor data, whether user motion is likely to lead to artifacts upon stress sampling. The exemplary method 1100 can return to block 1102 in response to a determination that user motion is not likely to lead to artifacts. The exemplary method can proceed to block 1114 in response to a determination that user motion is likely to lead to artifacts and can include modifying the sampling schedule.

Embodiments of the invention can provide real-time and/or continuous stress monitoring to a user. Embodiments of the invention can be useful in a variety of application areas, such as in work-based management, stress-management, health care applications, such as for autistic patients, for assistance and care of aging populations, for driver education and driver safety, and/or for academic situations. Embodiments of the invention can provide stress-aware continuous cycling.

In some embodiments of the invention, a training mode can be employed in which an individualized user stress profile is generated. In some embodiments of the invention, the individualized user stress profile is a generalized model that is updated and modified over time to become personalized to a user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention.

In this regard, each block in the flowchart or block diagrams may represent a module, segment, or portion of instructions, which comprises one or more executable instructions for implementing the specified logical function (s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for stress monitoring, the method comprising:
    receiving, by a processor, a plurality of user stress labels corresponding to a plurality of events;
    determining, by the processor, an individualized stress profile based at least in part upon the user stress labels by correlating a user identified stressor with an initial cardiovascular feature level;
    receiving, by the processor, heart rate sensor data from a wearable device;
    extracting, by the processor, a real-time cardiovascular feature from the heart rate sensor data;
    determining, by the processor, a stress index based at least in part upon the individualized stress profile and the cardiovascular feature, wherein the stress index provides a real-time determination of the presence or absence of an unhealthy stress level for the user; and
    outputting, by the processor, the stress index to the wearable device.

2. The computer-implemented method of claim 1 further comprising dynamically updating the individualized stress profile.

3. The computer-implemented method of claim 1 further comprising modifying the individualized stress profile based at least in part upon a recent stress.

4. The computer-implemented method of claim 1 further comprising receiving, by the processor, a motion artifact estimation.

5. The computer-implemented method of claim 4, wherein the motion artifact estimation is based at least in part upon motion sensor data.

6. The computer-implemented method of claim 1 further comprising receiving, by the processor, an individualized stress context.

7. The computer-implemented method of claim 6 further comprising modifying the individualized stress profile based at least in part upon the individualized stress context.

8. A computer program product for stress monitoring, the computer program product comprising:
    a computer readable storage medium readable by a processing circuit and storing program instructions for execution by the processing circuit for performing a method comprising:
    receiving a plurality of user stress labels corresponding to a plurality of events;
    determining an individualized stress profile based at least in part upon the user stress labels by correlating a user identified stressor with an initial cardiovascular feature level;
    receiving heart rate sensor data from a wearable device;
    extracting a real-time cardiovascular feature from the heart rate sensor data;
    determining a stress index based at least in part upon the individualized stress profile and the cardiovascular feature, wherein the stress index provides a real-time determination of the presence or absence of an unhealthy stress level for the user; and
    outputting the stress index to the wearable device.

9. The computer program product of claim 8, the method further comprising dynamically updating the individualized stress profile.

10. The computer program product of claim 8, the method further comprising modifying the individualized stress profile based at least in part upon a recent stress.

11. The computer program product of claim 8, the method further comprising receiving a motion artifact estimation.

12. The computer program product of claim 11, wherein the motion artifact estimation is based at least in part upon motion sensor data.

13. The computer program product of claim 8, the method further comprising receiving an individualized stress context.

14. The computer program product of claim 13, the method further comprising modifying the individualized stress profile based at least in part upon the individualized stress context.

15. A processing system for monitoring stress, comprising:
- a processor in communication with one or more types of memory, the processor configured to:
  - receive a plurality of user stress labels corresponding to a plurality of events;
  - determine an individualized stress profile based at least in part upon the user stress labels by correlating a user identified stressor with an initial cardiovascular feature level;
  - receive heart rate sensor data from a wearable device;
  - extract a real-time cardiovascular feature from the heart rate sensor data;
  - determine a stress index based at least in part upon the individualized stress profile and the cardiovascular feature, wherein the stress index provides a real-time determination of the presence or absence of an unhealthy stress level for the user; and
  - output the stress index to the wearable device.

16. The processing system of claim 15, wherein the processor is configured to dynamically update the individualized stress profile.

17. The processing system of claim 15, wherein the processor is configured to modify the individualized stress profile based at least in part upon a recent stress.

18. The processing system of claim 15, wherein the processor is configured to receive a motion artifact estimation.

19. The processing system of claim 18, wherein the motion artifact estimation is based at least in part upon motion sensor data.

20. The processing system of claim 15, wherein the processor is configured to receive an individualized stress context.

21. The processing system of claim 20, wherein the processor is configured to modifying the individualized stress profile based at least in part upon the individualized stress context.

22. A system for monitoring stress, comprising:
- a wearable device comprising:
  - a user interface configured to receive a plurality of user stress labels corresponding to a plurality of events;
  - a stress monitoring module comprising a heart rate sensor, an individualized stress profile, and a stress index engine, wherein the stress index engine is capable of determining a stress index for a user and the individualized stress profile based at least in part on the user stress labels by correlating a user identified stressor with an initial cardiovascular feature level; and
  - a sample regulation module comprising a sampling schedule controller, wherein the sample schedule controller is capable of actuating the stress monitoring module,
- wherein the heart rate sensor outputs heart rate sensor data indicative of a real-time cardiovascular feature, and
- wherein the stress index engine determines the stress index for the user during real-time based at least in part upon the individualized stress profile and the cardiovascular feature, and updates the individualized stress profile based at least in part on the stress-index.

23. The system of claim 22, further comprising an individualized stress context module.

24. The system of claim 23, wherein the individualized stress context module is in communication with the sampling schedule controller and the individualized stress profile.

25. A computer-implemented method for stress monitoring, the method comprising:
- activating, by a processor, a stress sampling based upon a sampling schedule;
- determining, by the processor, a heart rate variability based at least in part upon heart rate sensor data;
- determining, by the processor, an individualized stress profile based at least in part upon a user stress input;
- determining, by the processor, an continuous stress index based at least in part upon individualized stress profile and heart rate variability;
- receiving motion sensor data of a user; and
- modifying the sampling schedule based at last in part upon a determination that a user motion is likely to lead to artifacts.

* * * * *